US009467609B2

(12) United States Patent
White

(10) Patent No.: US 9,467,609 B2
(45) Date of Patent: Oct. 11, 2016

(54) MACHINE VISION INSPECTION SYSTEMS AND METHODS AND APERTURE COVERS FOR USE THEREWITH

(71) Applicant: Mettler-Toledo, LLC, Columbus, OH (US)

(72) Inventor: Timothy P. White, New Boston, NH (US)

(73) Assignee: Mettler-Toledo, LLC, Columbus, OH (US)

( * ) Notice: Subject to any disclaimer, the term of this patent is extended or adjusted under 35 U.S.C. 154(b) by 642 days.

(21) Appl. No.: 13/892,103

(22) Filed: May 10, 2013

(65) Prior Publication Data

US 2014/0333759 A1 Nov. 13, 2014

(51) Int. Cl.
*F21V 7/00* (2006.01)
*H04N 5/225* (2006.01)
*G01N 21/88* (2006.01)

(52) U.S. Cl.
CPC ........ *H04N 5/2256* (2013.01); *G01N 21/8806* (2013.01); *G01N 2021/8819* (2013.01)

(58) Field of Classification Search
CPC .................. G01N 21/8806; G01N 2021/8819
USPC ...................................... 362/350, 33, 296.02
See application file for complete search history.

(56) References Cited

U.S. PATENT DOCUMENTS

| | | | |
|---|---|---|---|
| 3,658,420 A | 4/1972 | Axelrod | |
| 5,060,065 A | 10/1991 | Wasserman | |
| 5,175,601 A | 12/1992 | Fitts | |
| 5,461,417 A | 10/1995 | White et al. | |
| 6,524,871 B2 | 2/2003 | Okawauchi | |
| 6,598,994 B1* | 7/2003 | Tait | G01B 11/00 362/11 |
| 7,041,997 B2* | 5/2006 | Paradis | G01N 21/8806 250/559.16 |
| 7,305,115 B2 | 12/2007 | King | |
| 7,557,920 B2* | 7/2009 | Lebens | G01N 21/21 356/394 |
| 7,773,209 B2 | 8/2010 | Hackney et al. | |
| 7,812,941 B2 | 10/2010 | Cameron et al. | |
| 7,877,003 B2 | 1/2011 | Dunn et al. | |
| 7,978,970 B2* | 7/2011 | Pastore | G03B 15/06 348/131 |
| 2001/0005264 A1 | 6/2001 | Slemon et al. | |
| 2004/0150815 A1* | 8/2004 | Sones | G01N 21/9054 356/239.4 |
| 2006/0091333 A1 | 5/2006 | Cochran et al. | |
| 2006/0180775 A1 | 8/2006 | Paradis | |
| 2009/0161208 A1 | 6/2009 | Kempe et al. | |
| 2010/0046826 A1 | 2/2010 | Dirix et al. | |
| 2010/0208980 A1 | 8/2010 | Urban et al. | |

FOREIGN PATENT DOCUMENTS

| | | |
|---|---|---|
| JP | 11-223851 A | 8/1999 |
| JP | 2003-224353 A | 8/2003 |
| JP | 2008-26149 A | 2/2008 |
| JP | 2010-19600 A | 1/2010 |

OTHER PUBLICATIONS

NET New Electronic Technology, LED illumination for Machine Vision, published prior to Oct. 1, 2011, 6 pages.

\* cited by examiner

*Primary Examiner* — Ali Alavi
(74) *Attorney, Agent, or Firm* — Standley Law Group LLP

(57) ABSTRACT

Machine vision inspection systems and methods for inspecting objects, such as objects with shiny surfaces, as well as illuminators with aperture covers for use therewith. Use of such an aperture cover eliminates the void (dark spot) in the illumination field that inherently results from the presence of an aperture through which an associated camera views an object to be inspected.

11 Claims, 5 Drawing Sheets

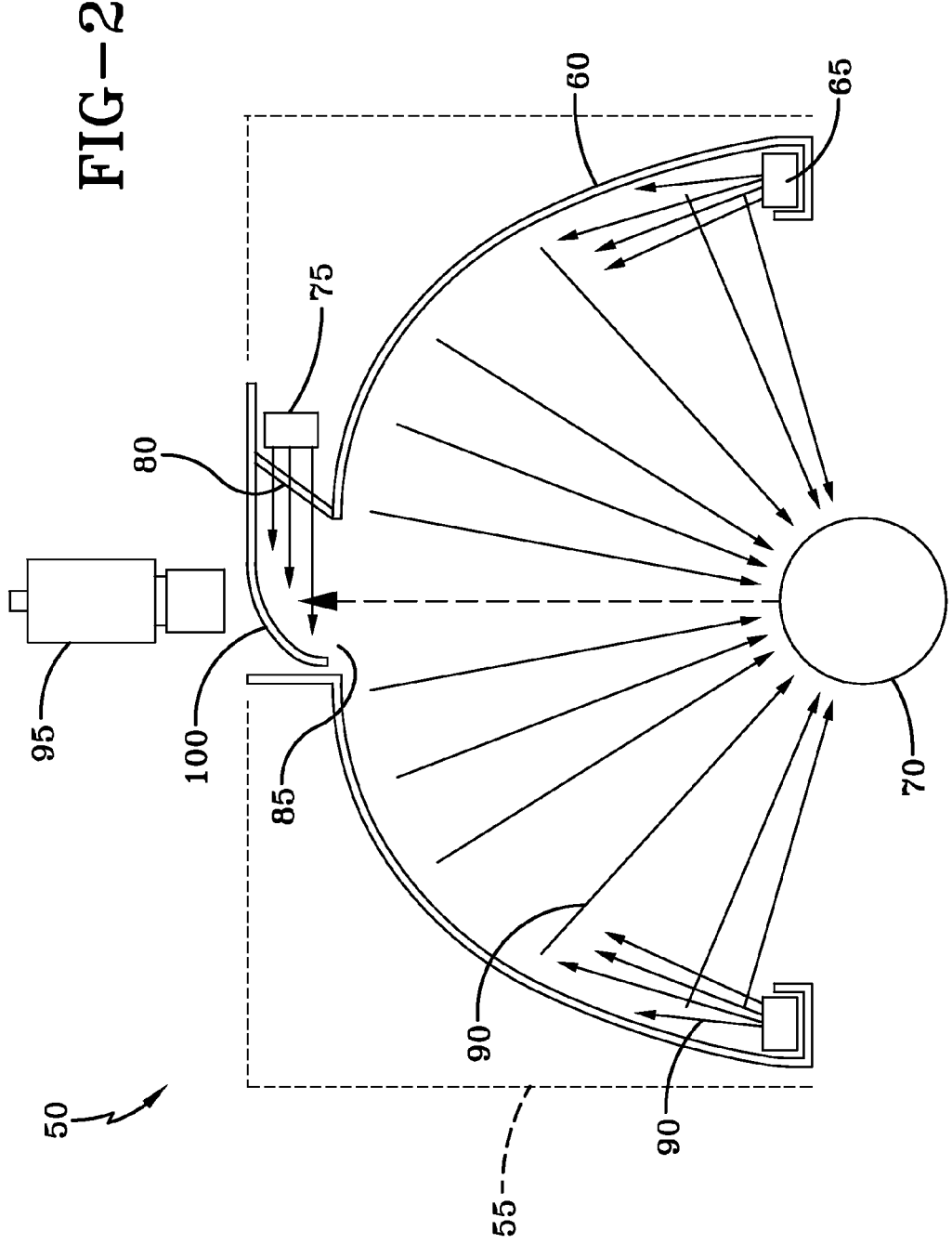

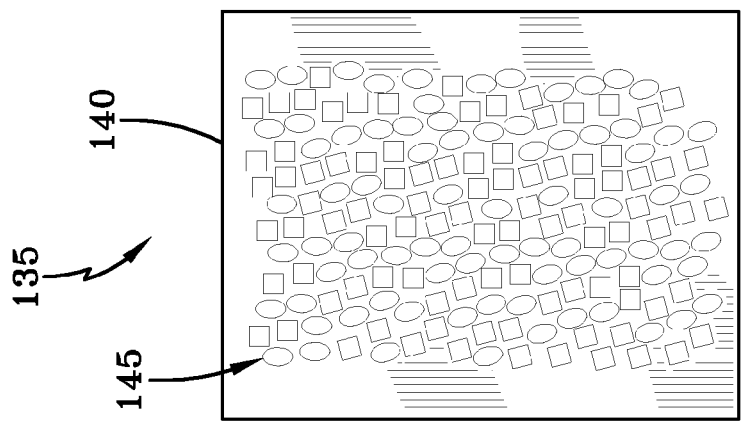
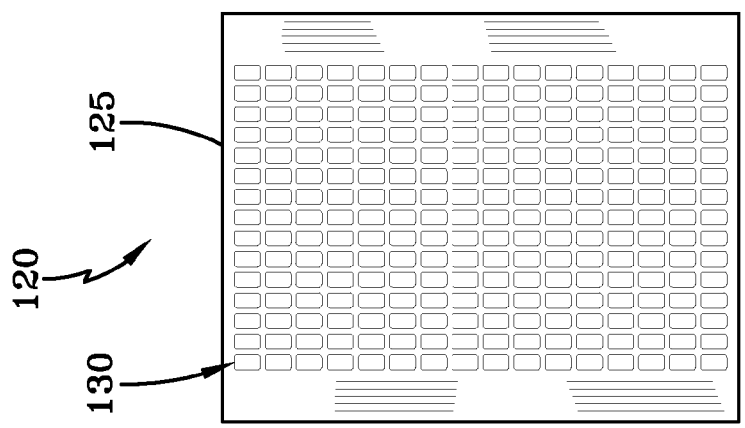
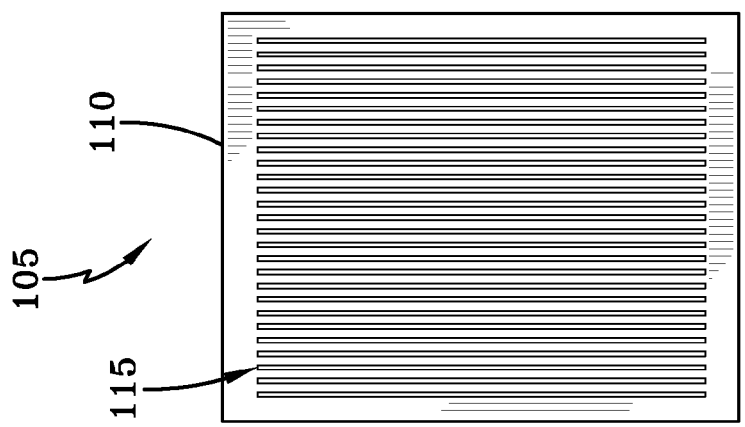

MACHINE VISION INSPECTION SYSTEMS AND METHODS AND APERTURE COVERS FOR USE THEREWITH

TECHNICAL FIELD

The present invention is directed to the field of machine vision inspection, particularly to the machine vision inspection of objects, such as objects with an irregular and/or specular surface.

BACKGROUND

Machine vision inspection of objects would be generally familiar to one of skill in the art. Systems and methods of machine vision inspection typically use one or more cameras and, frequently, one or more sources of illumination. Illumination may be provided in various forms including, but not limited to, direct illumination, back light illumination, ring illumination, horizontal illumination, coaxial illumination, and dome illumination.

When inspecting an object having a specular (shiny) surface, a super-diffuse illumination environment is particularly effective. Of the aforementioned illumination types, it has been found that dome illumination works very well for inspecting such objects, as well as objects having an irregular (e.g., convex, spherical, semi-spherical) shape. A machine vision inspection device that provides dome illumination is generally referred to as a dome illuminator.

As illustrated in FIG. 1, known dome illuminators typically include a hemispherical dome that overlies an object to be inspected (imaged). An illumination source, such as a ring of LEDs, is located within the dome. The interior surface of the dome is typically painted or otherwise coated with a diffusely reflective material such that light emitted by the illumination source is reflected off the dome and onto the object to be imaged.

Dome illuminators also include a central (axial) aperture that passes through the dome to provide a viewing window for an associated camera. The camera is focused on the upwardly facing surface of the object to be imaged, which surface is illuminated by the light being reflected off of the dome interior. An unfortunate side-effect of this design, however, is that the central aperture appears in reflection as a dark spot on the surface being imaged. This may result, for example, in an inability to read a code imprinted on the surface being imaged or an inability to see other features thereof.

A known solution to this problem is a device commonly referred to as a Cloudy Day® illuminator (CDI). A CDI typically includes a dome illuminator with a second co-axial light source that further illuminates an object to be inspected by projecting light through the central dome aperture. The brightness of the dome and co-axial light sources are balanced until they appear of equal brightness in reflection from the object surface being inspected.

While a CDI is an improvement over a typical dome illuminator, CDIs are expensive. Further, the addition of the co-axial light source adds to the size, and mechanical and electrical complexity of the dome illuminator, and also renders typical CDIs quite bulky. CDIs also employ a flat or curved beam splitter arrangement, which is usually fragile and difficult to clean.

It can be understood from the foregoing commentary that it would be desirable to provide a simple, cost-effective and compact machine vision inspection device that is capable of accurately imaging (inspecting) the entire specular surface of an object. Embodiments of the present invention are such devices.

SUMMARY

Embodiments of the invention provide substantially the same illumination uniformity as a CDI, but eliminate the complexity, added cost, and size. Embodiments of the invention are also able to eliminate the reflected dark spot problem referred to above with respect to the use of a typical dome illuminator. This is accomplished by making the reflected image of the central aperture of an illumination housing effectively disappear by covering the aperture with a diffusely reflective aperture cover.

An aperture cover according to the invention is, generally speaking, a cover adapted for placement over the central aperture of an illumination housing, with the cover containing an array of diffusely reflecting features interspersed between an array of very narrow slits that allow light to pass therethrough. The pattern of diffusely reflecting features and gaps may be arranged in a regular or irregular pattern.

With the cover in place over the central aperture, an associated camera is located close to the aperture cover. If the numerical aperture of the camera lens is held substantially wide open, the features of the aperture cover can be made to disappear in reflection, and the typical dark spot problem is eliminated. Embodiments of the invention can be further optimized by matching as closely as possible the reflectivity of the illumination housing interior and the aperture cover. The camera side of an aperture cover may also be coated with a non-reflective or substantially non-reflective material.

Other aspects and features of the invention will become apparent to those skilled in the art upon review of the following detailed description of exemplary embodiments along with the accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 2 schematically illustrates an exemplary embodiment of a typical cloudy day illuminator;

FIGS. 3A-3C show exemplary embodiments of aperture covers having regular and irregular patterns of the invention, for placement over the central aperture of an illumination housing;

DETAILED DESCRIPTION OF EXEMPLARY EMBODIMENT(S)

As discussed above, known dome illumination systems are used to inspect specular surfaces of objects of interest, but all suffer from an inherent void in the illumination field that results from the aperture through which the camera views the object being inspected. This void appears as a dark feature. "Healing" this void in the illumination field, to make it truly continuous, may be accomplished using a known Cloudy Day® illuminator (CDI) that makes use of a slanted or curved beam splitter illuminated by a secondary light source, which is balanced in brightness to match the surrounding illumination field. However, CDIs also have certain drawbacks, as mentioned above. Examples of a typical dome illuminator and a CDI are respectively depicted in FIG. 1 and FIG. 2.

Figure 1:
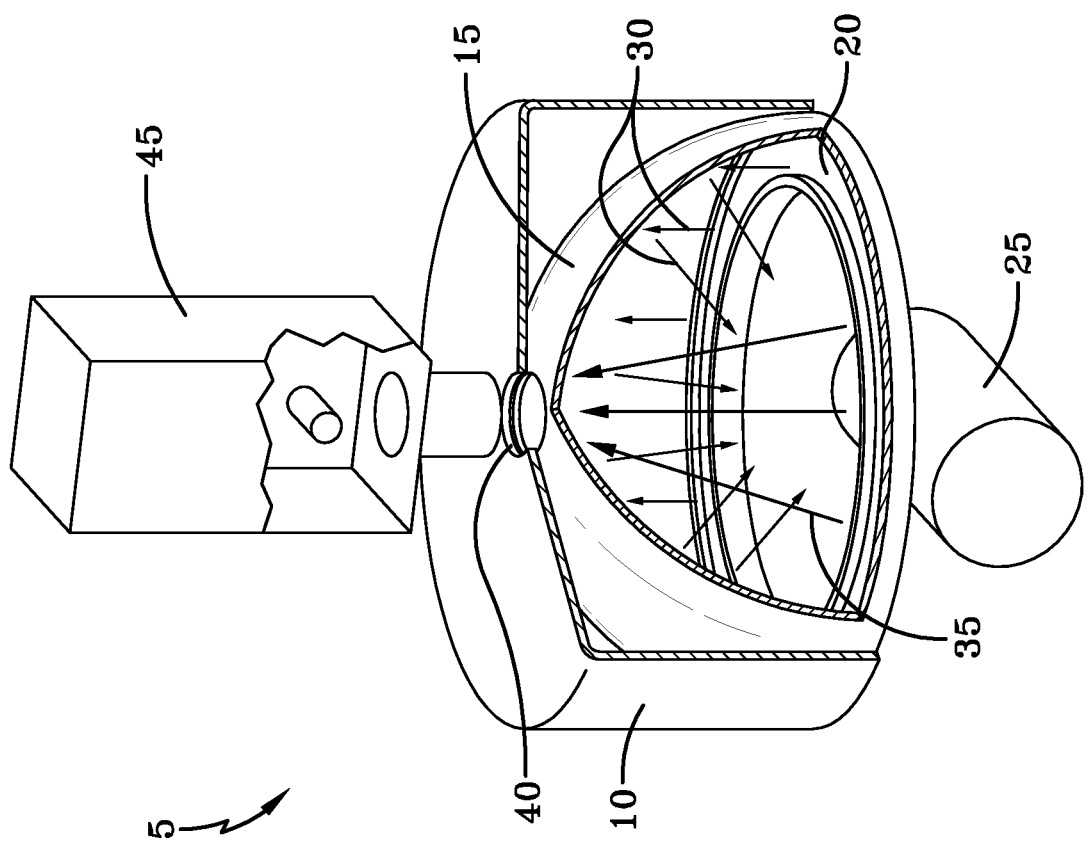
FIG. 1 is a partially cutaway view of a typical dome illuminator.

A typical dome illuminator 5 may be observed in FIG. 1. As shown, the dome illuminator 5 includes a substantially hollow illumination housing 10 with an open bottom. The interior of the illumination housing 10 forms a hemispherical diffuser 15. An illumination source 20, such as a ring light, a plurality of linear light sources, or an array of discrete LED light sources, is located near the base of the illumination housing 10 and is adapted to provide the illumination necessary to carry out an inspection process on an object 25 located below the illumination housing 10 and diffuser 15 portion thereof.

As can also be observed in FIG. 1, light rays 30 from the illumination source 20 are directed upward, where they are reflected with substantially equal brightness by the diffuser 15 back toward the object to be inspected. The desired surface of the object of interest 25 is thus indirectly illuminated 35 by the illumination source 20. A central aperture 40 passes through the illumination housing/diffuser 10, 15 such that the illuminated surface of the object of interest is made visible to an associated camera 45 located above the central aperture.

As described previously, a problem with such a dome illuminator is that the central aperture 40 will appear as a dark feature in the reflection of the object surfaces being imaged. Consequently, codes and/or other features of interest on the object surfaces being imaged may not be seen by the camera due to inadequate contrast.

A typical cloudy day illuminator (CDI) 50 designed to overcome the aforementioned problem with a dome illuminator is schematically illustrated in FIG. 2. As with the dome illuminator 5 exemplified in FIG. 1, the CDI 50 also includes a substantially hollow illumination housing 55 with an open bottom, the interior of the illumination housing forming a hemispherical diffuser 60. An illumination source 65, which may again be a ring light, is located near the base of the illumination housing 55 and is adapted to provide a portion of the illumination necessary to carry out an inspection process on an object of interest 70 located below the illumination housing and diffuser 60 portion thereof.

In comparison to the dome illuminator, however, the CDI 50 includes a second illumination source 75, which may be generally referred to as an on-axis or co-axial illumination source. The second illumination source 75 projects light through a beam splitter 80, which directs the light through a central aperture 85 in the illumination housing/diffuser 55, 60 and onto the surface of the object of interest 70.

As with the dome illuminator of FIG. 1, light rays 90 from the illumination source 65 are directed upward, where they are reflected with substantially equal brightness by the diffuser 60 back toward the object of interest 70. The desired surface of the object of interest 70 is thus indirectly illuminated by the illumination source 65 and directly illuminated by the second illumination source 75. Light from the object surface is reflected upward through the central aperture 85 to an associated camera 95 located above the illumination housing 55 where it forms part of the image. A clear (e.g., plastic) aperture 100 may be provided in the beam splitter arrangement to permit viewing of the object image by the camera 85.

As should be apparent from an observation of FIG. 2 and the above description, the additional components required to construct a CDI also make a CDI much more expensive than a typical dome illuminator. Furthermore, because of the beam splitter and associated structure commonly installed on the dome of a CDI, it is not possible to locate the inspection camera as close to the illumination housing as might be possible without the presence of such a secondary illumination source. This has the result of making a typical CDI quite bulky in comparison to a typical dome illuminator. Still further, the beam splitter arrangements commonly employed with a CDI are fragile and/or difficult to clean.

Therefore, embodiments of the invention are directed to machine vision inspection systems and methods that are inexpensive and compact in comparison to a CDI, but that produces CDI-like inspection results by eliminating the inherent void in the illumination field associated with a typical dome illumination-type devices. Generally speaking, this is accomplished through the use of an inspection device having an illumination housing equipped with a novel aperture cover that functions to fill the aperture void (dark spot) inherent to typical dome illuminators with a discontinuous pattern of opaque but diffusely reflecting features of very narrow dimension. These features may be thought of as sieve-like in nature with respect to the aperture covers and may be, for example, a series of slits which, when viewed in reflection from a specular surface of an object of interest, appear out-of-focus and blend into the surrounding illumination field.

Several exemplary and non-limiting aperture cover embodiments having various patterns of diffusely reflective features are shown in FIGS. 3A-3C. It is to be understood that the roughness (smoothness) of the surface being imaged, typically expressed as a root mean squared (RMS) dimension, largely determines the dimensions of the diffusely reflective features of the aperture cover. That is, the roughness of the surface being imaged will typically dictate that the diffusely reflective features fall within some limited range of dimensions in order for the diffusely reflective features to appear "invisible" to the camera in reflection off the surface. Generally speaking, the rougher the surface being imaged, the larger the diffusely reflective features may be. However, there is also a practical benefit to using smaller sieve aperture features—namely that surfaces having a greater range of surface roughness can be reliably imaged. Consequently, the diffusely reflective features of the exemplary aperture covers depicted in FIGS. 3A-3C are stated to fall within a particular dimension range or to be of a particular dimension. These dimension ranges and/or dimensions have been found to be particularly effective when used to image common surfaces to be inspected, such as the lids of typical metal cans. Nonetheless, other diffusely reflective feature dimension ranges or dimensions may be more suitable to the imaging of other surfaces.

In FIG. 3A, a first exemplary aperture cover 105 is shown to include a sheet of material 110 having a pattern of diffusely reflective features comprising a series of parallel, closely spaced, narrow slits 115 that pass therethrough. The number of slits 115, the width of the slits and the spacing between the slits may vary as explained above. In one non-limiting example, the width of the slits 115 may be between approximately 0.01 and 2.0 millimeters, more particularly between about 0.1 and 0.5 millimeters, and even more particularly, about 0.25 millimeters.

A second exemplary aperture cover 120 is shown in FIG. 3B to include a sheet of material 125 having a pattern of diffusely reflective features comprising a series of regularly recurring and substantially equidistantly-spaced holes 130 that pass therethrough. In this particular example, the holes 130 are shown to be substantially rectangular in shape, but various other shapes and other patterns are also possible. For example, such a regularly occurring pattern may take the form of a tessellation. The number of holes 130, the dimension(s) of the holes and the spacing between the holes may vary as explained above. In one non-limiting example, the minimum dimension of the holes 130 may be between approximately 0.01 and 2.0 millimeters, more particularly between about 0.1 and 0.5 millimeters, and even more particularly, about 0.25 millimeters.

A third exemplary aperture cover 135 is shown in FIG. 3C to include a sheet of material 140 having a pattern of diffusely reflective features comprising a multitude of non-repeating, substantially non-parallel and irregularly spaced holes 145 of various shape that pass therethrough. In this particular example, the holes 145 are shown to include various shapes (e.g., ellipses and squares), but various other shapes and combinations of shapes are also possible. The number of holes 145, the dimension(s) of the holes and the spacing between the holes may again vary as explained above. In one non-limiting example, the minimum dimension of the holes 145 may be between approximately 0.01 and 2.0 millimeters, more particularly between about 0.1 and 0.5 millimeters, and even more particularly, about 0.25 millimeters.

The size and shape of the exemplary aperture covers 105, 120, 135 of FIGS. 3A-3B are provided for purposes of illustration only and are not to be construed as limiting the invention to the relative dimensions and/or shapes shown. Aperture covers of other shapes such as, for example, circular shapes, could also be employed. Likewise, the pattern of the diffusely reflective features located in a given aperture cover, as well as the dimensions of the features, may vary as long as the effect thereof enables the aperture cover material to be rendered out-of-focus and, hence, substantially invisible to the inspection camera as described above and as illustrated and described in more detail below with respect to the embodiments of FIGS. 4-5. Similarly, aperture cover embodiments of the invention are not limited to manufacture from a particular material. The aperture cover pattern may also be formed directly in the dome material rather than as a separate piece attached thereto.

Figure 4:
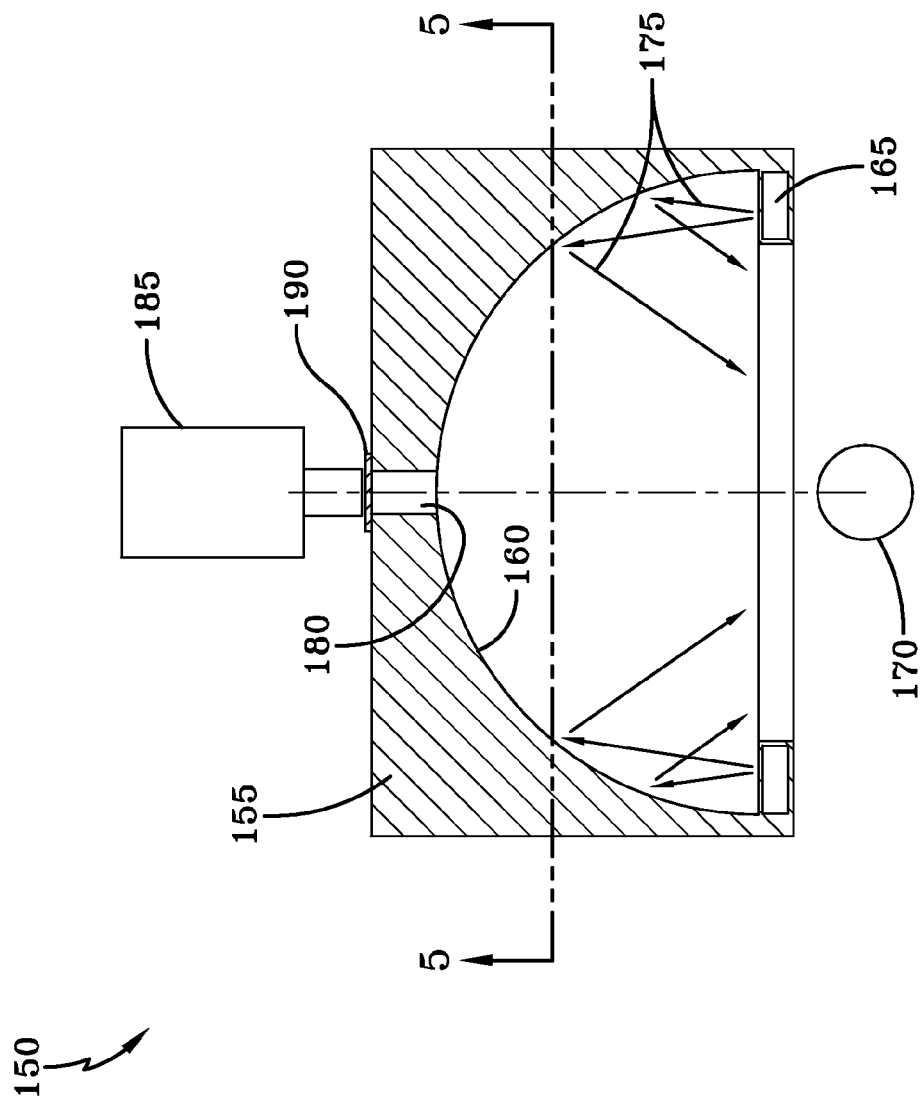
FIG. 4 is a simplified cross-sectional elevation view of a machine vision inspection device of the invention with an exemplary aperture cover located over the central aperture thereof.

A simplified cross-sectional elevation view of an exemplary embodiment of an inspection device 150 according to the invention is illustrated in FIG. 4. As shown, the inspection device 150 is similar to a typical dome illuminator and includes a substantially hollow body (illumination housing) portion 155 with an open bottom. The interior of the illumination housing 155 forms, in this case, a dome-shaped (e.g., hemispherical) diffusely reflective surface (diffuser) 160. Other diffuser shapes may also be possible in other embodiments as long as the selected shape results in a proper reflection of light onto an object of interest. For example, the reflective surface may be flat in certain embodiments.

An illumination source 165, such as a ring light, a plurality of linear light sources, or an array of discrete (e.g., point) light sources such as LEDs, is located near the base of the housing 160 and is adapted to provide the illumination necessary to carry out an inspection process on an object of interest 170 located below the illumination housing 155 and diffuser 160.

As previously described with respect to the known dome illuminator 5 of FIG. 1, light rays 175 from the illumination source 165 are directed upward, where they are reflected with substantially equal brightness by the diffuser 160 back toward the object of interest 170. The desired surface of the object of interest 170 is thus indirectly illuminated by the illumination source 165.

As also previously described with respect to the known dome illuminator 5 of FIG. 1, a central aperture 180 passes axially through the diffuser 160 and illumination housing 155 to provide an opening through which the object of interest 170 may be viewed with a camera 185. In a traditional dome illuminator, this would result in the central aperture appearing in reflection as a dark spot on the specular surface being inspected.

In order to overcome this dark spot problem, it can be observed in FIG. 4 that an exemplary aperture cover 190 of the invention is located over the central aperture 180 of the inspection device 150. The aperture cover 190 may be one of the exemplary aperture covers 105, 120, 135 depicted in FIGS. 3A-3C, or it may be of a different design. In any case, the camera 185 lens is located close to the aperture cover 190 and is operated at a wide aperture setting. As a result, the features of the aperture cover 190 are rendered out-of-focus and, hence, invisible to the inspection camera 185, despite the aperture cover material being substantially opaque. At the same time, the diffusely reflecting features of the aperture cover 190, when viewed in reflection from the specular surface of the object being inspected 170, appear out-of-focus and cause the reflected aperture 180 to blend into the surrounding illumination field, thereby eliminating the aforementioned dark spot problem. This allows for a more complete and accurate inspection of the specular surface of the object of interest.

Figure 5:
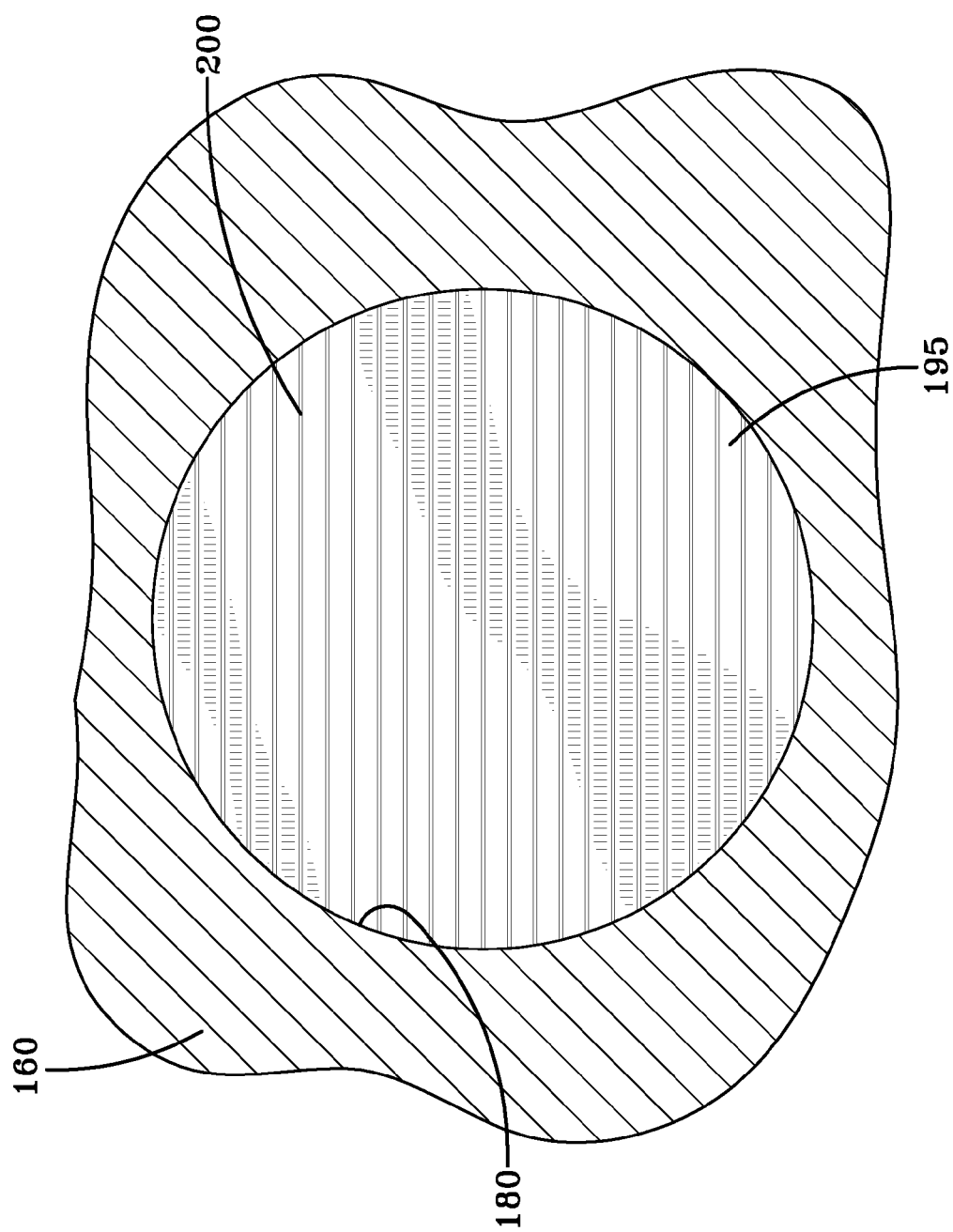
FIG. 5 is a bottom view of the machine vision inspection system of FIG. 4, wherein slits in the sieve aperture cover can be seen through the central aperture in the illumination housing.

For purposes of further illustration, an enlarged bottom view of the inspection device 150 of FIG. 4 is illustrated in FIG. 5. In this view, a portion of the aperture cover 190 is visible through the central aperture 180 in the illumination housing 155 of the inspection device 150. It can be observed that this particular exemplary aperture cover 190 is comprised of a sheet of material 195 that includes a series of parallel, closely spaced, narrow slits 200 that pass therethrough—much like the exemplary aperture cover 110 depicted in FIG. 3A. Such an array of narrow slits may be replaced by any pattern, regular or irregular, wherein the size of reflecting features and the gaps therebetween are small enough to be rendered substantially invisible in reflection as seen by the camera.

As previously explained, with the aperture cover 190 in place over the central aperture 180, the associated camera 185 is located close to the aperture cover. If the lens aperture of the camera 185 is held sufficiently open, the pattern of slits 200 in the aperture cover 190 may be made to disappear in reflection by being out of focus, and the dark spot that would typically represent the reflected image of the central aperture 180 is made to have substantially the same brightness as the surrounding diffuser 160 surface or to appear sufficiently similar in brightness to allow for reliable detection and imaging of surface features to be performed.

The results that can be produced by such an inspection device are quite adequate for typical optical character recognition (OCR) algorithms, and may be as good as or nearly as good as the results provided by a more complex and costly CDI. Additionally, inspection device embodiments of the invention can be further optimized by closely matching the reflectivity of the diffuser and the aperture cover. For example, the reflectivity of the diffuser may be slightly reduced and the reflectivity of the aperture cover material may be slightly increased, such that the apparent brightness in out-of-focus reflection of the diffuser and the aperture cover can be made to match as precisely as possible. Although not essential, the camera side of an aperture cover of the invention may also be coated with a non-reflective or substantially non-reflective material.

It should be understood that the choice of relative dome and aperture cover reflectivity may be flexible based on various factors, such as those described below, but obviously reaches an optimum when the out-of-focus apparent brightness of the aperture cover matches the apparent brightness of the surrounding surface. It has also been discovered that a high quality vision system using good edge-detection algorithms is relatively insensitive to a brightness mismatch in comparison to a typically cheaper but faster vision system using simplified brightness-threshold-based character segmentation algorithms. A better vision system, like a CIV, will thus be more insensitive to the potential difference in reflectivity between the diffuser and the aperture cover. Consequently, when used to examine common surfaces such as the lids of metal cans, it has been found, depending on the vision system employed, the range of surface roughness of the lids, etc., that the reflectivity of the diffuser may be within about ±75% of the average reflectivity of the aperture cover. In some embodiments, it may be preferable that the reflectivity of the diffuser is within about ±30% of the average reflectivity of the aperture cover and, in yet other embodiments, it may be preferable that the reflectivity of the diffuser is within about ±10% of the average reflectivity of the aperture cover.

While certain exemplary embodiments of the present invention are described in detail above, the scope of the invention is not to be considered limited by such disclosure, and modifications are possible without departing from the spirit of the invention as evidenced by the following claims:

What is claimed is:

1. A dome illuminator for the illumination of an object of interest, comprising:
    a substantially hollow housing with an open bottom, the interior of the housing forming a dome-shaped diffuser capable of reflecting light toward the open bottom thereof;
    an illumination source located near the open bottom of the housing and oriented to direct light onto the diffuser to create an illumination field;
    a central aperture providing a view, through the open bottom of the housing, of the object of interest; and
    an aperture cover located on the housing exterior and over the central aperture, the aperture cover having a discontinuous pattern of substantially opaque but diffusely reflective features oriented toward the open bottom of the housing.

2. The dome illuminator of claim 1, wherein the discontinuous pattern of substantially opaque but diffusely reflective features of the aperture cover comprises a plurality of substantially parallel and spaced apart narrow slits.

3. The dome illuminator of claim 2, wherein the width of each slit is between approximately 0.01-2.0 millimeters in minimum dimension.

4. The dome illuminator of claim 2, wherein the width of each slit is between approximately 0.1-0.5 millimeters in minimum dimension.

5. The dome illuminator of claim 2, wherein the width of each slit is approximately 0.25 millimeters in minimum dimension.

6. The dome illuminator of claim 1, wherein the discontinuous pattern of substantially opaque but reflective features of the aperture cover comprises an irregular non-parallel or non-repeating pattern of such features.

7. The dome illuminator of claim 1, wherein the discontinuous pattern of substantially opaque but reflective features of the aperture cover comprises a regular repeating tessellation or pattern.

8. The dome illuminator of claim 1, wherein the reflectivity of the diffuser is within about ±75% of the average reflectivity of the aperture cover.

9. The dome illuminator of claim 1, wherein the reflectivity of the diffuser is within about ±30% of the average reflectivity of the aperture cover.

10. The dome illuminator of claim 1, wherein the reflectivity of the diffuser is within about ±10% of the average reflectivity of the aperture cover.

11. The dome illuminator of claim 1, wherein a camera side of the aperture cover is coated with a non-reflective, substantially non-reflective, or substantially opaque material.

* * * * *